Siekmann

[11] 4,303,376
[45] Dec. 1, 1981

[54] FLOW METERING CASSETTE AND CONTROLLER

[75] Inventor: Rem Siekmann, Barrington, Ill.

[73] Assignee: Baxter Travenol Laboratories, Inc., Deerfield, Ill.

[21] Appl. No.: 55,898

[22] Filed: Jul. 9, 1979

[51] Int. Cl.³ .................. A61M 5/00; F04B 9/12; F04B 43/06
[52] U.S. Cl. ......................... 417/360; 417/384; 417/395; 417/474; 417/479; 417/510; 417/518; 128/214 F
[58] Field of Search ............... 417/383, 384, 385, 386, 417/387, 388, 395, 360, 474, 476, 510, 518, 520, 478, 479; 128/214 F, DIG. 12

[56] References Cited

U.S. PATENT DOCUMENTS

| | | | |
|---|---|---|---|
| 2,308,974 | 1/1943 | Harper | 417/510 |
| 2,356,738 | 8/1944 | Brugger | 417/510 X |
| 3,045,601 | 7/1962 | Rippingille | 417/360 X |
| 3,151,783 | 10/1964 | Shaw et al. | 222/335 |
| 3,252,623 | 5/1966 | Corbin et al. | 222/59 |
| 3,654,959 | 4/1972 | Kassell | 137/4 |
| 3,697,197 | 10/1972 | Berglund et al. | 417/360 |
| 3,800,794 | 4/1974 | Georgi | 128/214 E |
| 4,046,610 | 9/1977 | Lilja | 512/523 |
| 4,121,584 | 10/1978 | Turner et al. | 128/214 E |
| 4,142,524 | 3/1979 | Jassawalla et al. | 128/214 F |
| 4,199,307 | 4/1980 | Jassawalla | 417/474 |

FOREIGN PATENT DOCUMENTS

| | | | |
|---|---|---|---|
| 2233320 | 1/1973 | Fed. Rep. of Germany | 417/510 |
| 2723197 | 12/1977 | Fed. Rep. of Germany | 128/214 F |
| 2639992 | 3/1978 | Fed. Rep. of Germany | 128/214 F |
| 1204103 | 9/1970 | United Kingdom | 417/518 |

Primary Examiner—Leonard E. Smith
Attorney, Agent, or Firm—Paul C. Flattery; John A. Caruso; Eugene M. Cummings

[57] ABSTRACT

A cassette and controller for accurately controlling fluid flow through an administration set while maintaining a closed fluid system. Inlet and outlet conduits are defined in a body of the cassette and inlet and outlet valves control fluid flow through the respective conduits. A rigid internal cavity of predetermined volume is also defined in the cassette body with an impermeable and flexible diaphragm spanning the cavity. A control conduit communicates with the internal cavity on an opposite side of the diaphragm from the fluid to alternately exert negative and positive pressure on the diaphragm. Negative pressure causes the diaphragm to conform to the shape of the internal cavity when the inlet valve is open to fill the cavity-shaped diaphragm with fluid from the inlet conduit. Positive pressure against the diaphragm expels fluid from the cavity through the outlet conduit when the outlet valve is opened. A controller for the cassette provides the positive and negative pressures and controls the inlet and outlet valves. Related methods of metering the fluid through the cassette are also disclosed.

8 Claims, 13 Drawing Figures

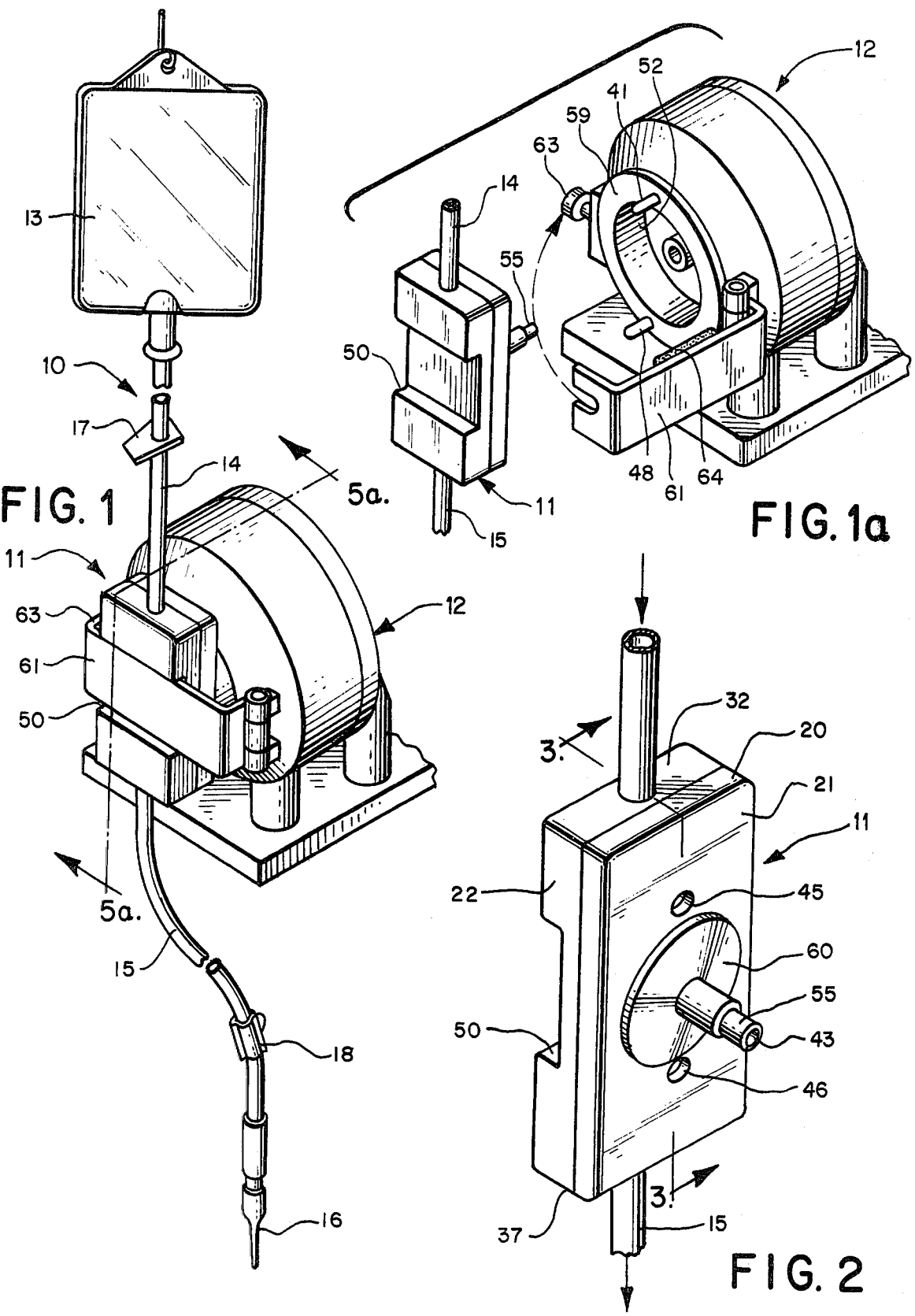

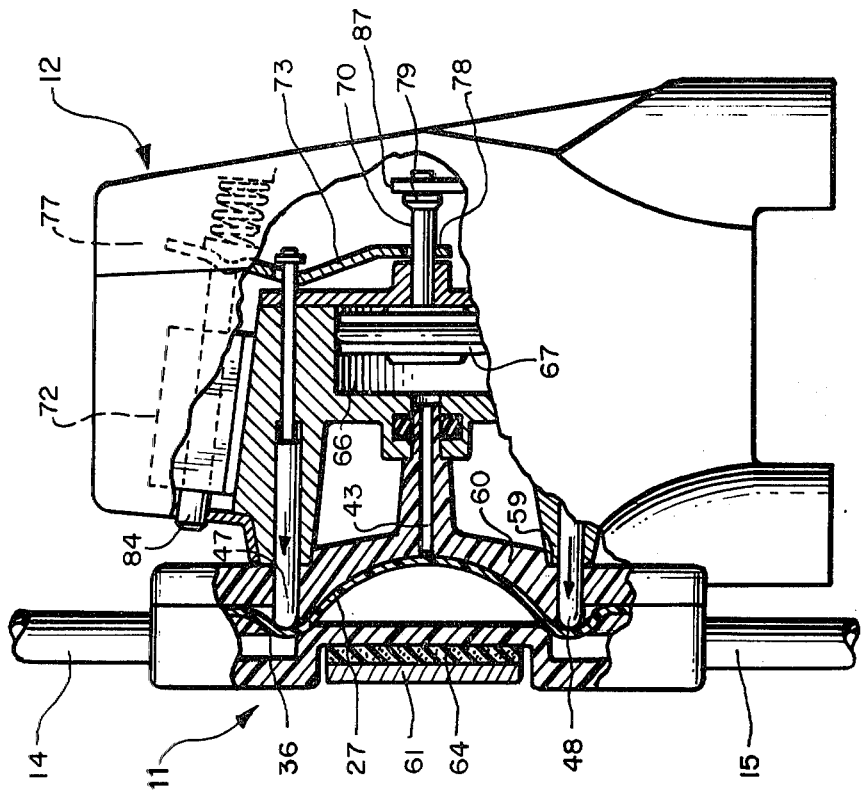
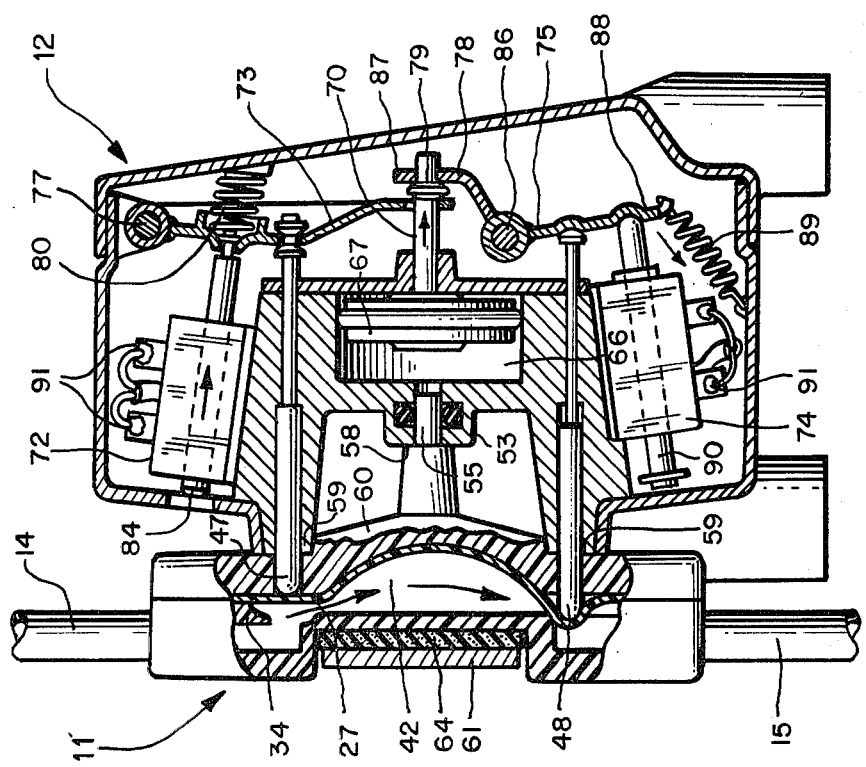

FLOW METERING CASSETTE AND CONTROLLER

BACKGROUND OF THE INVENTION

This invention relates in general to apparatus for pumping controlled quantities of fluid through a closed fluid system, and is more particularly concerned with a cassette for incorporation into an administration set for accurately metering the volume of parenteral fluid flowing through the administration set, and with a controller for controlling fluid flow through the cassette.

In recent years, the need has arisen for apparatus for controlling the rate of administration of parenteral fluids to a patient with a high degree of accuracy while maintaining a closed fluid system to avoid the possibility of contamination of the infused fluids.

One type of apparatus utilized for accurately metering fluid flow in a closed system utilizes a cassette-type pump element included as an integral component of the flow system, together with a controller mechanism which actuates the pump element at a predetermined rate to establish a desired flow rate within the system. After use, the cassette element is disengaged from the controller mechanism, and discarded with the flow system, thereby avoiding the possibility of contamination of subsequently administered liquids.

The present invention is directed to a cassette and controller which provides improved metering accuracy, and which can be economically manufactured by known manufacturing techniques.

SUMMARY OF THE INVENTION

A cassette constructed in accordance with the invention comprises a body having inlet and outlet conduits defined therein, inlet and outlet valves disposed in the respective inlet and outlet conduits, an internal cavity of preselected and known volume, a flexible and impermeable diaphragm disposed across and spanning the cavity, and a control conduit communicating with the internal cavity. In metering fluid through the cassette, negative pressure is first introduced in the control conduit to act upon the diaphragm. The inlet valve is then opened and as the diaphragm begins to conform to the shape of the internal cavity, fluid is accumulated in the cavity-shaped diaphragm. The inlet valve is closed when the diaphragm is filled. Thereafter, the outlet valve is opened and a source of positive pressure is introduced in the control conduit to act upon the diaphragm to expel the fluid from the cavity-shaped diaphragm as the diaphragm begins to assume its unflexed shape. When all of the fluid from the pumping cycle is thereby expelled from the cassette, the outlet valve is closed and the metering cycle may begin anew.

To aid in filling and emptying fluid trapped by the diaphragm in the internal cavity, a channel is preferably disposed between the inlet and outlet valves such that the diaphragm does not trap pockets of fluid between the conduits in the cassette, but totally expels fluid from the internal cavity through the channel.

Since the internal cavity is of preselected and known volume, the amount of fluid metered through the cassette bears direct relation to the number of metering cycles. Likewise, the rate of metering is dependent upon the number of metering cycles within a known time interval. Greater control and accuracy over the volume of fluid infused or the rate of infusion is attained since the constant volume of the internal cavity controls the volume of fluid metered through the cassette. The internal cavity also minimizes the effects of temperature, fluid viscosity, and ambient atmospheric pressure upon the accuracy of fluid metered through the cassette, in contrast to prior art metering devices which depend upon resilient or deformable elements for control of volume. The metering accuracy is further enhanced by provision of a valving system which does not cause deflection of the diaphragm in the vicinity of the internal cavity which could otherwise affect the volumetric measuring performance of the internal cavity.

The cassette may be fabricated from simple and inexpensive materials, such as thermoplastic materials, such that economy of manufacture or use is not compromised. In this regard, the cassette will ordinarily be a disposable item along with the administration set such that a new and sterile administration set, including a cassette, may be used for each and every infusion. Since a minimum of parts are used in the cassette, reliability is not sacrificed.

The invention is further directed to controller apparatus for controlling the cassette in accurately metering the fluid flowing therethrough. The controller has receiving means for receiving the control conduit of the cassette into the controller, sealing means disposed between the receiving means and the control conduit to provide a pneumatic seal therebetween, and means for alternatively applying positive and negative pressures in the control conduit of the cassette. Typically, the positive and negative pressure means would include a piston slidably disposed in a cylinder with an annular seal disposed therebetween and means for moving the piston in a reciprocating manner to alternately change the pressure in the control conduit from positive to negative. The controller may also have a pair of valving pins received by apertures in the cassette to depress or release the diaphragm from respective inlet and outlet valve regions of the inlet and outlet valves to control flow of the fluid through the inlet and outlet conduits. The controller further includes means for periodically operating the inlet and outlet valving pins and the piston such that the positive and negative pressure created by the piston are in synchronization with opening and closing of the inlet and outlet valves during the aforedescribed metering cycle. The valving pins and piston will typically be operated by pivotal arms which are solenoid actuated, with the solenoids controlled by timing circuitry.

The invention is also directed to the methods of metering fluid through the cassette by the controller apparatus including the basic steps of providing negative pressure in the control conduit to urge the diaphragm to conform to the shape of the internal cavity, opening the inlet valve to permit fluid flow through the inlet conduit into the cavity-shaped diaphragm, closing the inlet valve, changing the pressure in the control conduit from negative to positive, opening the outlet valve to permit the positive pressure in the control conduit to urge the diaphragm to resume its normal shape and thereby expel fluid through the outlet conduit, and closing the outlet valve when the fluid has been expelled from the cassette.

BRIEF DESCRIPTION OF THE DRAWINGS

The features of the present invention, which are believed to be novel, are set forth with particularity in the appended claims. The invention, together with the further advantages thereof, can best be understood by reference to the following description taken in conjunction with the accompanying drawings, in the several figures in which like reference numerals identify like elements, and in which:

FIG. 1 is an elevational perspective view of the cassette and controlling apparatus of the present invention illustrating a typical administration set for infusing fluids from a fluid bag which contains a source of fluid to be infused through the administration set and the cassette, which is incorporated therein, and which is secured to the controller apparatus;

FIG. 1a is an exploded perspective view of the cassette and the controller apparatus of FIG. 1 illustrating the connection of the cassette to the controller; or the disconnection therefrom;

FIG. 2 is a perspective view of an opposite side of the cassette from that shown in FIGS. 1 and 1a;

FIG. 5a is an elevational view, with the controller taken substantially in section along line 5a—5a of FIG. 1 and the cassette partially broken away to illustrate the cassette operatively engaged with the controller during a portion of the metering cycle when negative pressure created by the controller causes the diaphragm to conform to the shape of the internal cavity such that the cavity-shaped diaphragm is filled with fluid from the inlet conduit through the open inlet valve while the outlet valve remains closed;

FIG. 5b is an elevational view of the cassette and the controller both partially broken away, similar to FIG. 5a but with the inlet valve closed to trap fluid in the cavity-shaped diaphragm;

DESCRIPTION OF A PREFERRED EMBODIMENT

Figure 3:
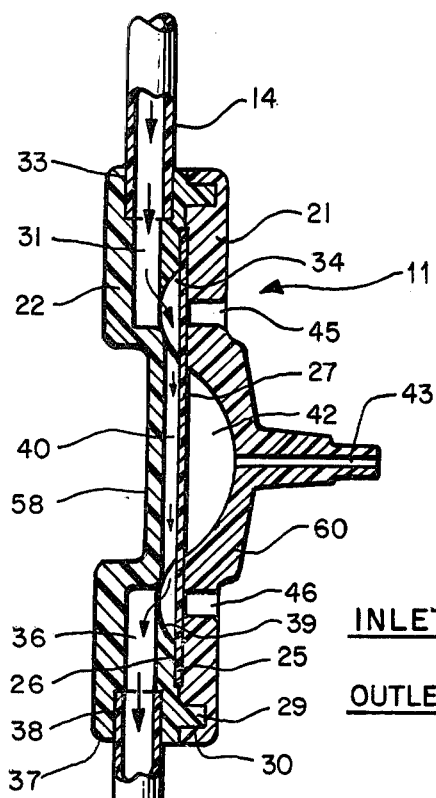
FIG. 3 is a sectional view of the cassette taken along line 3—3 of FIG. 2 illustrating the direction of fluid flow through the cassette, and other internal structural features, including the internally disposed diaphragm and the internal cavity of the cassette.

Referring first to FIG. 1, there is illustrated an administration set, generally designated 10, with a cassette, generally designated 11, incorporated in the administration set 10 in accordance with the invention for pumping and accurately metering the volume of parenteral fluid or blood flowing through the administration set. Cassette 11 is illustrated in operative engagement with a controller, generally designated 12, also in accordance with the invention, and as more fully described hereinafter.

Besides cassette 11, the administration set 10 typically includes a flask or bag 13 which contains a volume of parenteral fluid, blood or the like to be infused into a patient, a length of tubing 14 communicating between bag 13 and an inlet end of cassette 11, another length of tubing 15 communicating between an outlet end of cassette 11 and an appropriate needle 16 or the like. Suitable clamps 17, 18 may be provided on respective tubing segments 14, 15 for separately and independently controlling or stopping the flow of fluid through the administration set by controlling the degree of constriction of tubing segments 14, 15. Cassette 11 also be may be provided with a pointed inlet tip (not shown) adapted to puncture and establish fluid communication with sealed tubing or fluid containers, if so desired, and an enlarged gripping lobe or collar (not shown) circumferentially surrounding a portion of such an inlet tip to aid in gripping the inlet tip while puncturing the tubing or container.

As is better illustrated in FIG. 1a, cassette 11 may be readily engaged or disengaged from controller 12. Cassette 11 is designed to maintain a closed fluid system such that the fluid pumped by cassette 11 remains sterile and otherwise uncontaminated. It is therefore contemplated that each administration set will be provided with a cassette 11 incorporated therein. As will be more fully appreciated hereinafter, the design and construction of the cassette permits inexpensive manufacture such that each administration set may be readily and inexpensively disposed of after use.

On the other hand, the controller 12 may be used repeatedly to control the flow of fluid through each new cassette 11 and administration set 14. Because of the single and disposable uses of cassette 11 and the repeated use of controller 12, the present invention further provides for a convenient, economical and efficient interface and connection between cassette 11 and controller 12.

Figure 4:
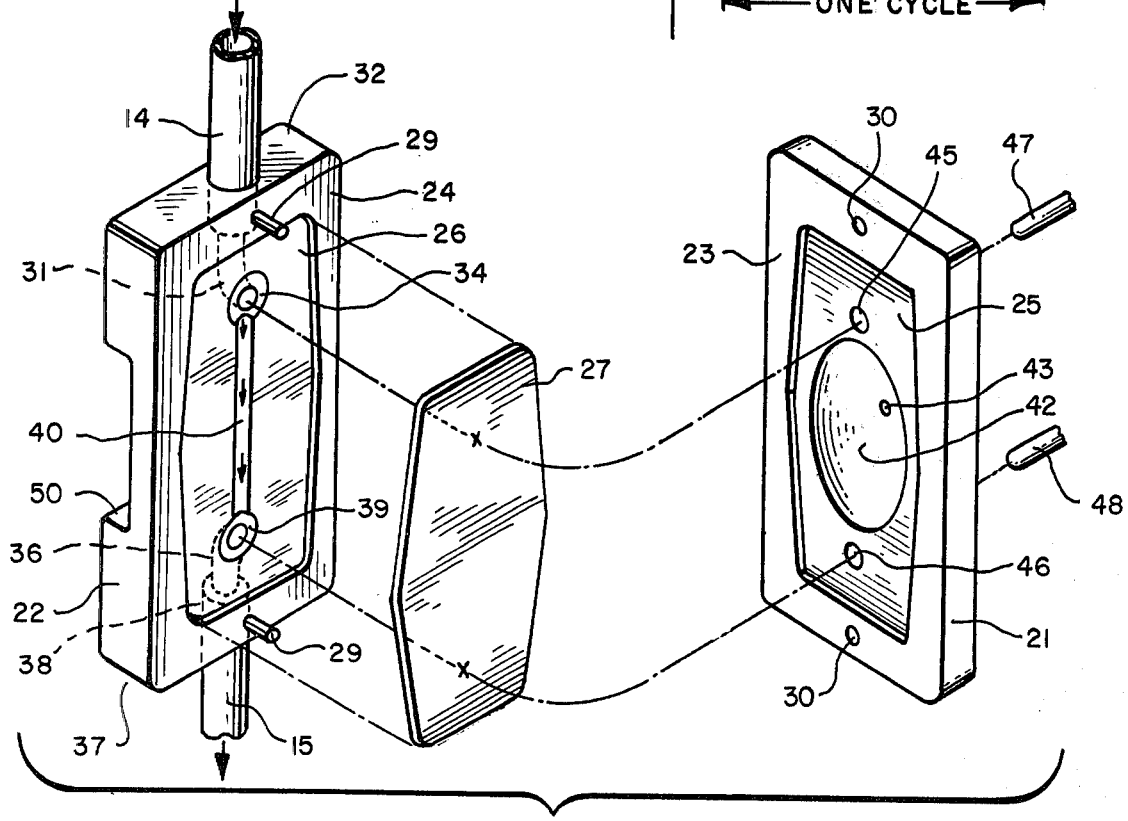
FIG. 4 is an exploded perspective view of mating portions of the cassette with the diaphragm disposed therebetween.

With reference to FIGS. 2, 3 and 4, the preferred embodiment of cassette 11 is illustrated in greater detail. Cassette 11 has a body 20 which is divided into a front portion 21 and a rear portion 22 with portions 21, 22 each having a respective generally planar mating surface 23, 24 defined about the periphery of portions 21 and 22. A shallow recess 25 of generally oval shape is defined in mating surface 23 of front portion 21, with a similar recess 26 defined in mating surface 24 of rear portion 22 for receiving therein an impermeable and flexible diaphragm 27. The sum of the depths of recesses 25 and 26 is preferably equal to or slightly less than the thickness of diaphragm 27 for compressively securing diaphragm 27 therebetween when front and rear portions 21, 22 are matingly assembled. Guide means in the form of pegs 29 projecting from mating surface 24 of rear portion 22, and corresponding apertures 30 in mating surface 23 of front portion 21, are provided for precisely aligning front and rear portions 21, 22 of body 20, and for retaining the portions in alignment thereafter.

Rear portion 22 of cassette body 20 in combination with diaphragm 27 provides a closed fluid flow system. The periphery of diaphragm 27 is preferably bonded or ultrasonically welded to the correspondingly shaped periphery of recess 26 to insure the integrity of the closed fluid system. An inlet fluid conduit 31 is defined in an inlet end 32 and includes a larger diameter bore 33 for sealingly receiving one end of inlet tubing segment 14 of administration set 10. Defined in recess 26 near one of the oval shaped ends thereof is a concave or dish-shaped inlet valve region 34. Inlet conduit 31 provides fluid communication between inlet tubing segment 14 and inlet valve region 34.

In a similar manner, an outlet fluid conduit 36 is defined in an outlet end 37 of back portion 21. Conduit 36 has an increased diameter bore 38 for sealingly receiving one end of outlet tubing segment 15. A concave or dish-shaped outlet valve region 39 is defined in the recess 26 at an opposite end of the oval-shaped recess from inlet valve region 34. Outlet fluid conduit 36 provides fluid communication between outlet tubing segment 15 and outlet valve region 39.

Defined in recess 26 between inlet valve region 34 and outlet valve region 39 is a channel 40 of generally semicircular cross-section. Channel 40 provides a path for gravity flow of fluid through the administration set between inlet valve region 34 and outlet valve region 39 when it is not desired to use cassette 11 in conjunction with controller 12. For example, it may be desirable to administer gravity flow of the fluid contained in flask or bag 13 to a patient until a certain volume of fluid has been administered and to thereafter meter the volume of fluid being administered by using cassette 11 in conjunction with controller 12. Channel 40 also aids in filling and emptying diaphragm 27 with fluid by acting as an extension of inlet conduit 31 for filling of diaphragm 27 and by preventing pockets of fluid from being trapped between the diaphragm and recess 26 during emptying of fluid from cassette 11. In this regard, channel 40 acts as an extension of outlet conduit 36.

A dome-shaped cavity 42 is defined in recess 25 at a generally central location therein. Diaphragm 27 spans the large open end of cavity 42. It is important that cavity 42 not be oppositely disposed from any portion of inlet valve region 34 or outlet valve region 39 when front and back body portions 21, 22 are in mating engagement. Under such conditions, cavity 42 defines a known and preselected volume and is independent of operation of either valve region 34 or 39. In gaseous communication with cavity 42 is a control conduit 43 to alternately apply positive and negative pressures in control conduit 43 and hence in internal cavity 42 to act upon that portion of diaphragm 27 encompassed by internal cavity 42. It is understood that negative pressure refers to pressure less than the ambient atmospheric pressure, i.e. partial vacuum, and that positive pressure refers to air pressure greater than the ambient atmospheric pressure. Under the influence of negative pressure in control conduit 43 and cavity 42, that portion of diaphragm 27 encompassed by cavity 42 will tend to conform to the shape of internal cavity 42 to provide a cavity-shaped portion of diaphragm 27 into which a known and preselected volume of fluid may be admitted into cassette 11 through inlet conduit 31, inlet valve region 34, and that portion of channel 40 which is in fluid communication with inlet valve region 34. Under the influence of positive pressure in control conduit 43 and internal cavity 42, diaphragm 27 will tend to resume its normal generally planar shape to expel fluid previously accumulated in the cavity-shaped portion of diaphragm 27 through that portion of the channel 40 which is in fluid communication with outlet valve region 39 and through outlet conduit 36 into outlet tubing segment 15.

As previously discussed, cassette 11 permits free gravity flow of fluid therethrough when not installed in controller 12. Therefore, to control the flow of fluid through cassette 11 during sequencing of pressure in control conduit 43, means must be supplied to control the flow of fluid through the inlet valve region 34 and outlet valve region 39 at appropriate timing intervals in synchronization with change of pressure in control conduit 43. To this end, an inlet valve aperture 45 and an outlet valve aperture 46 are defined through front body portion 21 at respective positions which are in alignment with respective inlet and outlet valve regions 34, 39, but on an opposite side of diaphragm 27 therefrom. As seen in FIG. 4, an inlet valving pin 47 and an outlet valving pin 48 may be inserted through respective inlet and outlet valve apertures 45, 46 to depress or release portions of diaphragm 27 overlying respective inlet and outlet valve regions 34, 39 to thereby open or close respective inlet or outlet fluid conduits 31, 36. Valving pins 47, 48 have rounded ends for depressing diaphragm 27 against respective inlet and outlet valve regions 34, 39 to provide an appropriate fluid seal thereat. The rounded ends also avoid puncture of the diaphragm 27 while operating thereagainst.

A transverse recess 50 is defined in an external surface of back portion 22, opposite mating surface 24, to aid in positioning and securing cassette 11 in controller 12 as is best seen in FIGS. 1 and 1a.

The cassette is designed to be simply and economically manufactured from thermoplastic materials by known thermoplastic molding techniques. Only a small amount of material is required since the cassette typically has a maximum external dimension of less than three inches (7.62 centimeters) which further enhances the disposability and single use function of the cassette. Diaphragm 27 may be easily cut or molded from latex or similar elastomers.

It will be understood that various means of applying alternating positive and negative pressure in control conduit 43 of cassette 11 may be employed. Preferably, a controller 12 is utilized for this purpose since, as will be better appreciated hereinafter, the necessity of supplying separate positive and negative pressure sources with appropriate and synchronized valving is thereby avoided. With reference to FIGS. 1a and 5a through 5d, a portion of the exterior surface of controller 12 which mates with cassette 11 is provided with an annular recess 52. Disposed in annular recess 52 is an annular boss 53 with a bore 54 extending therethrough and adapted for receiving therein a tapered end 55 of control conduit 43 of cassette 11. An O-ring 56 or other suitable sealing means is disposed in an annular recess 57 defined in bore 54 to suitably seal against tapered end 55 of control conduit 43. The exterior surface of control conduit 43 also has an abrupt abutment 58 to stop against boss 53 when end 55 of control conduit 43 is inserted into bore 54 to the appropriate depth. An annular exterior housing portion 59 (FIG. 1a) disposed about annular recess 52 of controller 12 has a generally planar surface for engaging against front body portion 21 of cassette 11 about a cavity housing 60 (FIGS. 2 and 5a) to further aid in centering cassette 11 in controller 12.

Other means of controlling diaphragm 27 include the use of alternating external sources of pressure and vacuum in place of the action of a reciprocating piston 67. Alternatively, direct mechanical coupling to diaphragm 27 could be utilized for movement of same in internal cavity 42.

After the cassette 11 is inserted into controller 12 for operative engagement therewith, a clamping strap 61 (FIGS. 1 and 1a) is pivoted into recess 50 in rear body portion 22 of cassette 11 to lockingly secure the cassette to the controller. Means of retaining clamping strap 61 in the locked position, such as a locking screw 63 or the like, may be utilized. A layer of resilient material 64 on the inside of clamping strap 61 engages against cassette 11 in recess 50 to dampen any vibrations which may occur such as those due to operation of controller 12.

Approximately centrally disposed in controller 12 and in gaseous communication with bore 54 is a cylinder 66 with a piston 67 slidably disposed therein. An O-ring 68 about the annular periphery of the piston 67 creates a suitable gaseous seal between piston 67 and the cylinder 66 for creation of air pressures in cylinder 66 on the compression side of piston 67 at bore 54 and control conduit 43. The other end of cylinder 66 is preferably open, as by apertures 69, to minimize the amount of work needed to move piston 67. The side of piston 67 opposite the compression side has a stem 70 attached thereto and adapted to move the piston.

Slidably disposed in controller 12 on opposite sides of piston 67 are valving pins 47 and 48 which project outwardly through annular housing 59 to be received in respective inlet and outlet valve apertures 45, 46 of cassette 11 when the cassette is in operative engagement with the controller.

Figure 6:
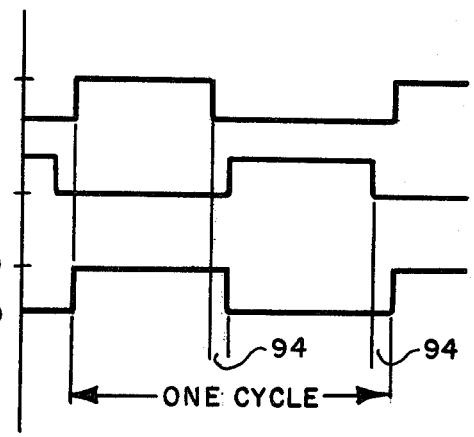
FIG. 6 is a schematic diagram of the timing relationships between the inlet valve and outlet valve of the cassette and the piston of the controller for one metering cycle.

While various means of operating valving pins 47, 48 and piston 67 will be apparent to those skilled in the art, operating means which simultaneously operate both valving pins 47, 48 and piston 67 in the timing relationship evidenced in FIG. 6 is desired to synchronize operation of piston 67 with valving pins 47, 48. The preferred embodiment of controller 12 is best illustrated in FIGS. 5a through 5d. An inlet solenoid 72, in combination with an inlet arm 73, controls the position of inlet valving pin 47 and causes retraction of piston 67 in the cylinder 66 to provide negative pressure in control conduit 43 during those portions of the metering cycle when the inlet valve is open. An outlet solenoid 74 and a pivotable outlet arm 75 control the position of outlet valving pin 48 and cause the piston 67 to provide positive pressure in control conduit 43 during those portions of the metering cycle when valving pin 48 is open.

Figure 5C:
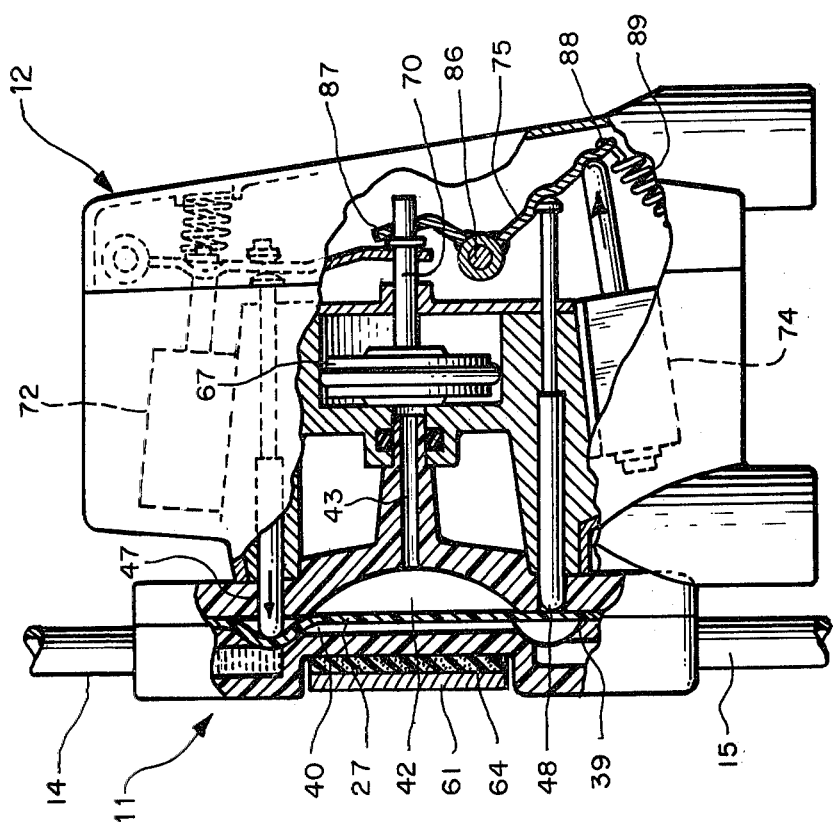
FIG. 5c is an elevational view of the cassette and controller partially broken away, similar to FIG. 5b, but with the outlet valve now open and with the controller exerting positive pressure on the diaphragm of the cassette to begin urging the diaphragm to resume its normal planar shape and thereby expel the fluid through the outlet valve and the outlet conduit.
Figure 5D:
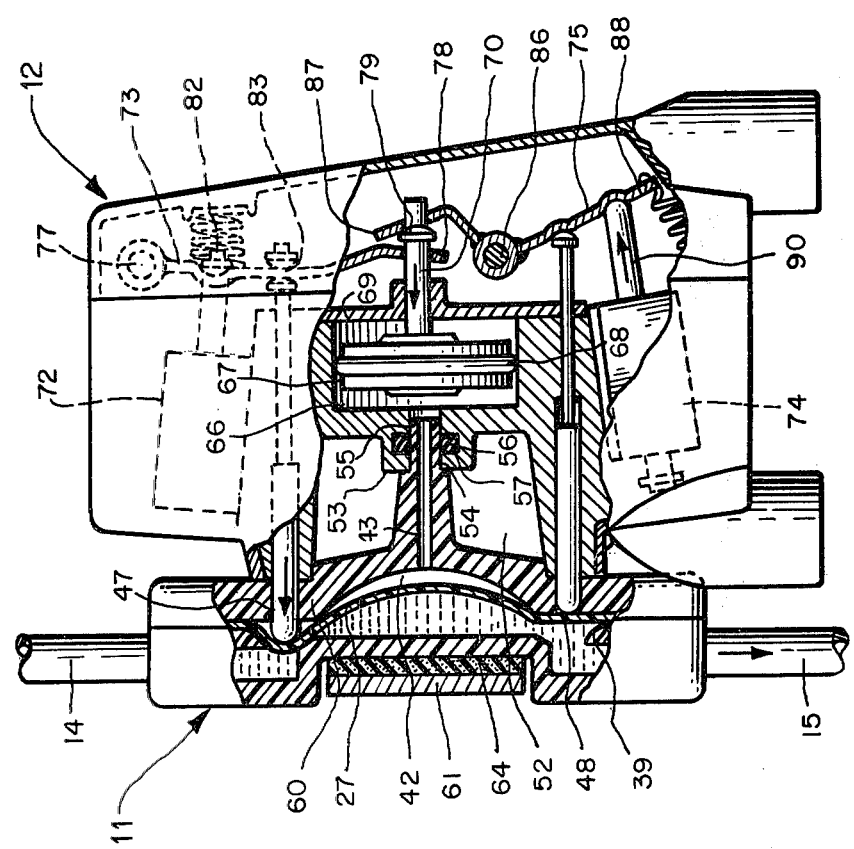
FIG. 5d is an elevational view of the cassette and controller partially broken away, similar to FIG. 5c, but with the diaphragm having resumed its normal planar shape upon expelling the fluid from the cassette such that the outlet valve may now be closed and the metering cycle may begin anew.

One end 77 of inlet control arm 73 is pivotally secured to controller 12 with an opposite end 78 slidably disposed about stem 70 between piston 67 and a catch or detent 79 affixed to stem 70. A compression spring 80 normally biases valving pin 47 against diaphragm 27 to keep inlet valve region 34 in a closed condition as seen in FIGS. 5b through 5d. When inlet solenoid 72 is energized, as seen in FIG. 5a, an armature 84 of solenoid 72 overcomes the bias of spring 80 to pivot inlet arm 73 toward spring 80 and away from solenoid 72. This pivotal movement of arm 73 causes piston 67 to retract and thereby create negative pressure in control conduit 43 such that the portion of diaphragm 27 encompassed by internal cavity 42 assumes the cavity shape in FIG. 5a. At the same time, inlet valving pin 47, which is pivotally secured to inlet control arm 73 about point 83, moves out of inlet valve region 34 to permit fluid flow therethrough. Upon de-energization of inlet solenoid 72, biasing of spring 80 pivots inlet arm 73 and thereby causes inlet valving pin 47 to close inlet valve area 34. However, due to the slidable connection of end 78 of control arm 73 about stem 70, inlet control arm 73 can cause retraction of piston 67 at appropriate times in the metering cycle by exertion of force against detent 79, but cannot cause a compression stroke of piston 67. Piston 67 therefore remains in the retracted position.

Outlet control arm 75 is both structurally and functionally different. A pivot point 86 is located intermediate one end 87, which is slidably disposed about stem 70 of piston 67, but on the opposite side of detent 79 from end 78 of inlet control arm 73. An opposite end 88 of outlet control arm 75 is biased by tension in a spring 89 to urge outlet valving pin 48 against diaphragm 27 to keep outlet valve region 39 in a closed condition. Energization of outlet control solenoid 74 moves an armature 90 thereof against end 88 to open outlet valving pin 48. Both outlet valving pin 48 and solenoid 74 are provided with pivotal connections along end 88 so as not to interfere with or limit the pivoting action of outlet control arm 75. Solenoids 72 and 74 each have a pair of electrical terminals 91 for electrical connection to controlling and timing circuitry (not shown) which supplies an electrical energization characteristic in accordance with the timing diagram of FIG. 6. The timing circuitry will preferably have an adjustable duty cycle or repetition rate such that controller 12 can provide a wide range of flow rates through cassette 11 for a predetermined volumetric size of internal cavity 42.

From the timing diagram of FIG. 6, it can be seen that controller 12 utilizes a timing characteristic wherein both the inlet and outlet valves are closed or only one of the valves is open. It is preferable that at least one valve always be closed to prevent unmeasured or unregulated gravity flow through the cassette. It is therefore essential that short timing intervals, identified by reference numeral 94, occur before opening of either the inlet or the outlet valves during which both of the valves are closed, and that both the inlet and outlet valves be closed prior to the changing of pressure exerted by the piston from positive to negative, or vice versa.

The metering operation of cassette 11 in conjunction with controller 12 through one complete cycle is best seen in FIGS. 5a through 5d. In FIG. 5a, energization of inlet solenoid 72 causes armature 84 to pivot inlet control arm 73, which in turn retracts piston 67 in cylinder 66 to cause diaphragm 27 to assume the shape of internal cavity 42 and thereby draw fluid through inlet valve region 34 past inlet valving pin 47, which was simultaneously opened by pivotal movement of inlet control arm 73. During filling of that portion of diaphragm 27 which has assumed the cavity shape, outlet valving pin 48 remains closed such that accumulation of fluid in cavity-shaped diaphragm 27 occurs only through the inlet.

In FIG. 5b, inlet control solenoid 72 has been de-energized thereby causing arm 73 to slidably move inlet valving pin 47 to close inlet valve region 36 by depressing a portion of diaphragm 27 thereagainst. At the same time, apertured end 78 of inlet control arm 73 slidably moves along stem 70 of piston 67 without changing the retracted position of the piston and the pressure in control conduit 43 therefore remains unchanged when inlet valve region 36 is closed. A measured volume of liquid is thereby accumulated and momentarily trapped in cavity-shaped diaphragm 27 between the closed inlet and outlet valves.

In FIG. 5c, outlet control solenoid 74 has now been energized, causing outlet valving pin 48 to slidably move away from and open outlet valve region 39. At the same time, piston 67 begins a compression stroke to change the pressure exerted against cavity-shaped diaphragm 27 from negative to positive with reference to the ambient atmospheric pressure. Fluid previously trapped in the cavity-shaped diaphragm is thereby gradually expelled from cassette 11 through outlet tubing 15. During this period of time, the inlet valve remains closed such that the volume of liquid previously trapped in cassette 11 is all expelled through the outlet valve.

In FIG. 5d, diaphragm 27 has resumed its normal generally planar shape in spanning interval cavity 42 upon all of the fluid being expelled through the outlet valve. Accordingly, outlet control solenoid 74 is de-energized to permit return spring 89 to return outlet control arm 75 to its normal position. Outlet valving pin 48 thereby depresses diaphragm 27 against outlet valve region 39 and apertured end 87 of control arm 75 slidably moves along stem 70 of piston 67 to keep piston 67 in the compressed position. A complete pumping cycle has now been completed and upon energization of inlet control solenoid 72, as illustrated in FIG. 5a, the metering cycle may begin anew.

Inherent in the above description of the various relationships and functions of the constituent elements of cassette 11 and controller 12 were methods of accurately controlling the volume of fluid flowing through the cassette in a closed fluid system. The basic method of controlling fluid flow through cassette 11 of the above-described type includes the successive steps of providing negative pressure in control conduit 43 to urge diaphragm 27 to conform to the shape of internal cavity 42, opening the inlet valve to permit fluid to flow through inlet conduit 31 into cavity-shaped diaphragm 27, closing inlet valve region 34, changing the pressure in control conduit 43 from negative to positive, opening outlet valve region 39 to permit the positive pressure in control conduit 43 to exert pressure on diaphragm 27 to urge the diaphragm to resume its normal planar shape and thereby expel fluid through outlet conduit 36, and closing outlet valve region 39 when fluid has been expelled upon the diaphragm resuming its normal shape. This basic method may be periodically repeated to pump a preselected and known volume of fluid for each cycle. Opening and closing of inlet and outlet valve regions 34, 39 may be accomplished by alternately releasing and depressing portions of diaphragm 27 which overly the respective inlet and outlet valve regions, as by means of inlet and outlet valving pins 47, 48. Alternation of pressure in control conduit 43 from positive to negative may be accomplished by a controller 12 of the above-described type.

Figure 8:
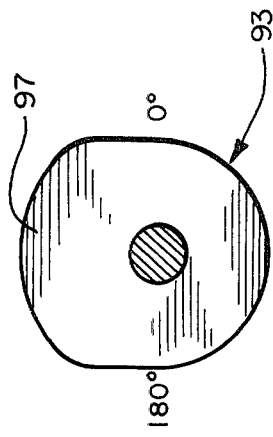
FIG. 8 is an enlarged plan view of one of the cams in FIG. 7 further illustrating the lobe design of each cam.
Figure 9:
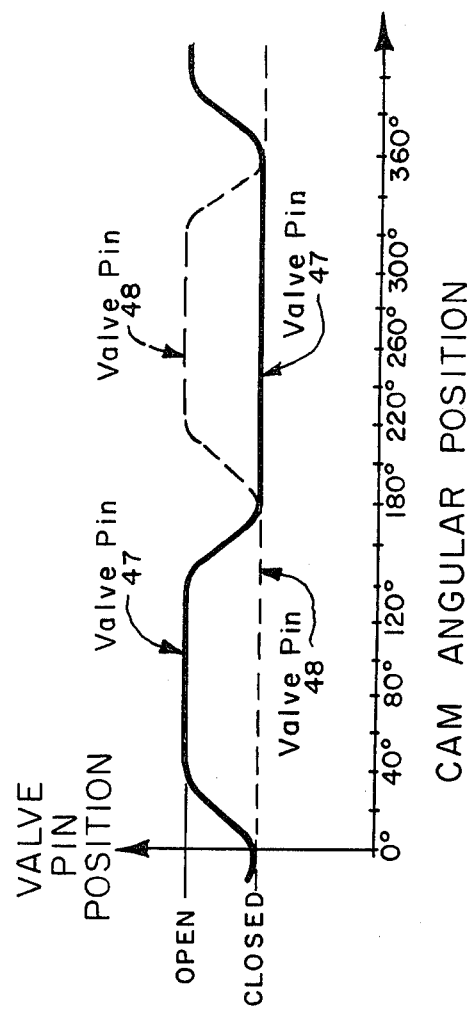
FIG. 9 is a graphic diagram illustrating operation of each cam in FIG. 7 in controlling one metering cycle of the cassette.
Figure 7:
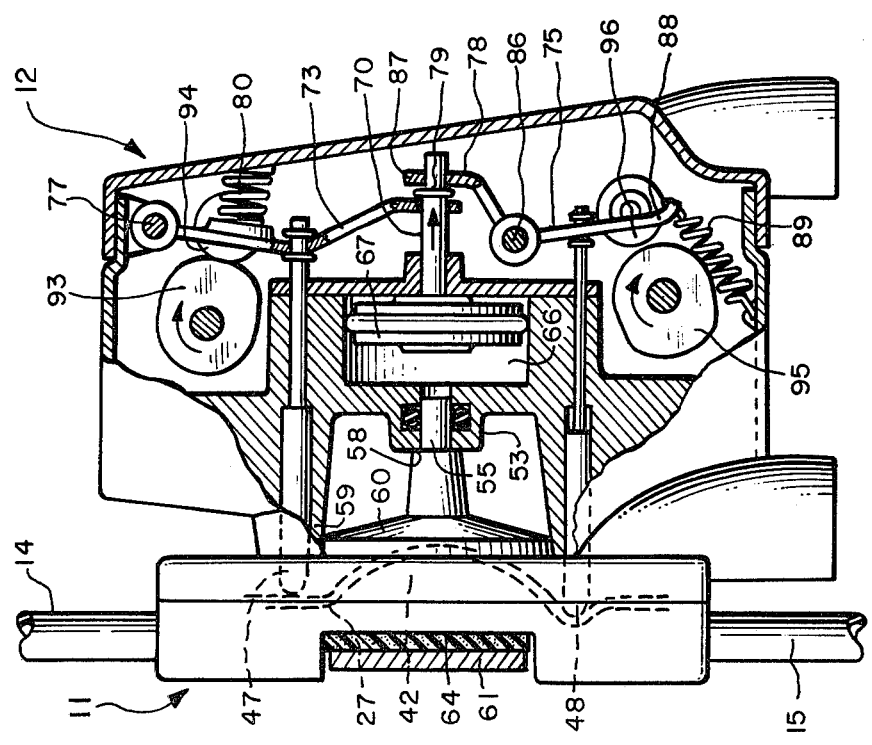
FIG. 7 is an elevational view similar to FIG. 5a, illustrating cams operatively adapted to control fluid flow through the cassette, instead of solenoids as in FIGS. 5a through 5d.

Other means of actuating piston 67 and the inlet and outlet valves 34 and 39 will be readily apparent to those skilled in the art. For example, piston 67 and valving pins 47 and 48 could be controlled by other means of pivotally moving inlet control arm 73 and outlet control arm 75. To this end, in FIG. 7 an inlet control cam 93 is rotatably mounted in the controller 12 adjacent to the inlet control arm 73. Cam 93 rotatably engages a follower wheel 94 which is rotatably mounted in the control arm 73. In a like manner, an outlet control cam 95 is rotatably mounted in the controller 12 adjacent to the outlet control arm 75. Cam 95 rotatably engages a follower wheel 96 which is mounted for free rotation in outlet control arm 75. Cams 93 and 95 each have a lobe 97 (FIG. 8) adapted to control the position of the respective valving pins 47 and 48 in accordance with the timing diagram in FIG. 9. That is, lobe 97 for each of cams 93 and 95 is designed such that a common driving means, such as an electric motor (not shown), for cams 93 and 95 causes respective valving pins 47 and 48 to fully close before the other valving pin is opened. It is also important that the lobes 97 be designed to provide sufficient time for filling of cavity 42 with fluid when valving pin 47 is in an open position and sufficient time for emptying of fluid from cavity 42 when valving pin 48 is in an open position. While follower wheels 94 and 96 are preferred to reduce friction with respective cams 93 and 95, it will be readily apparent that cams 93 and 95 may alternatively slidably contact respective control arms 73 and 75.

Similarly, it will be apparent that cassette 11 could utilize other types of inlet and outlet valves, such as check valves which could also be separate from the cassette, as in the inlet and outlet tubing.

While a particular embodiment of the invention has been shown and described, it will be obvious to those skilled in the art that changes and modifications may be made without departing from the invention in its broader aspects, and, therefore, the aim of the appended claims is to cover all such changes and modifications as fall within the true spirit and scope of the invention.

I claim:

1. Flow control apparatus for a fluid flow system comprising a removable flow controlling cassette and a controller for actuating the cassette,
    said cassette comprising:
    a control conduit;
    an inlet conduit and an outlet conduit, said inlet and outlet conduits including respective valve portions closable in response to an applied mechanical force;
    metering means comprising a metering chamber in fluid communication with said inlet and outlet conduits and having a volume dependent on an applied pressure effect in said control conduit;
    said controller comprising:
    a housing defining means for receiving the cassette in an operating position;
    an actuator conduit;
    means comprising a cylinder and piston assembly in said housing in pressure communication with said actuator conduit, said piston being movable between first and second positions within said cylinder to produce a pressure control effect in said actuator conduit, said piston assembly including a piston rod;
    pressure seal means for forming a separable pressure seal between said actuator conduit and said cassette control conduit when the cassette is in said operating position;
    first actuator means comprising a first mechanical actuator member in said housing in operative engagement with said inlet conduit when said cassette is in said operating position and actuable to open said inlet conduit and move said piston toward said first position;

second actuator means comprising a second mechanical actuator member in said housing in operative engagement with said outlet conduit when said cassette is in said operating position and actuable to open said outlet conduit and move said piston toward said second position, said first and second actuator means comprising respective valve actuator members slidably mounted for reciprocation within said controller housing for operative engagement with said valve portions, said valve actuator members actuating said valve portions closed except on actuation of said first and second actuator means when said cassette is in said operating position, said first and second actuator members being engaged to said piston rod, said first actuator member being pivotally mounted to said housing at one end, and engaged to said piston rod at its other end, and operatively engaged to said inlet valve actuator member intermediate said ends, and said second actuator arm being engaged to said piston rod at one end, operatively engaged to said outlet valve actuator rod at its other end, and pivotally mounted to said housing intermediate its ends, and metering control means for alternately actuating said first and second actuator members and said piston whereby said inlet and outlet conduits are alternately opened and closed and said metering chamber is alternately expanded and contracted to pump fluid through the system.

2. Flow control apparatus as defined in claim 1 wherein said actuator members are slidably engaged to said piston rod, and wherein collar means fixedly attached to said piston rod are provided between said first and second actuator arms for actuating said piston in one direction upon actuation of said first actuator arm, and in the opposite direction upon actuation of said second actuator arm.

3. Flow controller apparatus for actuating in a fluid flow system a flow controlling cassette of the type having a housing defining an internal cavity, inlet and outlet conduits, and a control conduit;

means including a fluid-impermeable diaphragm in the cavity responsive to an applied pressure control effect in the control conduit for forming a metering chamber of controllable volume in fluid communication with the inlet and outlet conduits; and inlet and outlet valve means associated with said inlet and outlet conduits and selectively actuable to control fluid flow therein whereby metered flow is established in the administration set with changes in the volume of the metering chamber;

said controller apparatus comprising:

a housing including means for receiving the cassette in an operating position;

valve control means comprising parallel-spaced inlet and outlet valve actuator members slidably mounted in said housing for actuating upon axial displacement thereof respective ones of said valve means;

means including a piston cylinder and piston in said housing in pressure communication with said control conduit for producing with reciprocative movement of said piston a pressure control effect in said control conduit, said piston including a piston rod extending therefrom;

means including a first actuator arm pivotally mounted to said housing at one end, and slidably engaged to said piston rod at its other end, and operatively engaged to said inlet valve actuator member intermediate said ends, said actuator arm actuating said inlet valve actuator to close said inlet valve upon rotation of said arm from a first position to a second position about said pivot;

means including a second actuator arm slidably engaged to said piston rod at one end, operatively engaged to said outlet valve actuator member at its other end, and pivotally mounted to said housing intermediate its ends, said actuator arm actuating said outlet valve actuator to close said outlet valve upon rotation of said arm from a first position to a second position about said pivot;

collar means fixedly attached to said piston rod between said first and second actuator arms for actuating said piston in end direction upon actuation of said first actuator arm from said second to said first position, and in the opposite direction upon actuation of said second actuator arm from said first to said second position; and inlet and outlet actuator means for alternately actuating said first and second actuator arms whereby the cassette metering chamber is alternately caused to fill through said inlet valve and discharge through said outlet valve to establish fluid flow through the flow system.

4. Controller apparatus as defined in claim 3 wherein said inlet actuator means and said outlet actuator means respectively comprise an inlet solenoid and an outlet solenoid, said solenoids being electrically energizable to respectively move said inlet actuator arm and said outlet actuator arm.

5. Controller apparatus as defined in claim 3 wherein said inlet actuator means and said outlet actuator means respectively comprise an inlet cam and an outlet cam, said cams being rotatable to respectively cause movement of said inlet actuator arm or said outlet actuator arm.

6. Controller apparatus as defined in claim 5 wherein each cam has a lobe defining a lift surface of less than 180° on each of said cams, said cams being rotatably driven such that said inlet valve control means and said outlet valve control means are not simultaneously retracted to permit unregulated fluid flow through said cassette.

7. Controller apparatus as defined in claim 3 including biasing means for biasing said first and second actuator arms to said second positions, and wherein said inlet and outlet actuator means actuate said arms to said first positions, whereby the inlet and outlet valve means of the cassette are actuated closed in the absence of actuation of said actuator arms.

8. Controller apparatus as defined in claim 7 wherein said biasing means comprise first and second spring members respectively associated with said first and second actuator arms.

* * * * *